United States Patent [19]

Lübbers et al.

[11] 4,003,707
[45] Jan. 18, 1977

[54] METHOD AND ARRANGEMENT FOR MEASURING THE CONCENTRATION OF GASES

[75] Inventors: Dietrich W. Lübbers; Norbert Opitz, both of Dortmund, Germany

[73] Assignee: Max-Planck-Gesellschaft zur Forderung der Wissenschaften e.V., Munich, Germany

[22] Filed: Feb. 26, 1976

[21] Appl. No.: 661,636

[30] Foreign Application Priority Data

Feb. 28, 1975 Germany .................... 2508637

[52] U.S. Cl. .................... 23/232 R; 23/254 R; 356/39; 356/85
[51] Int. Cl.[2] ................ G01J 3/30; G01N 21/26; G01N 21/48; G01N 33/16
[58] Field of Search ........ 23/232 R, 232 E, 254 R, 23/254 E; 356/39, 85

[56] References Cited

UNITED STATES PATENTS

| | | | |
|---|---|---|---|
| 3,734,691 | 5/1973 | Kukla et al. | 23/254 R X |
| 3,754,867 | 8/1973 | Guenther | 23/232 R X |
| 3,830,222 | 8/1974 | Chance | 356/39 X |

Primary Examiner—Robert M. Reese
Attorney, Agent, or Firm—Michael J. Striker

[57] ABSTRACT

A method and an arrangement for measuring the concentration of gases in a sample includes the generation of a monochromatic light beam having predetermined color characteristic. An indicator generates light signals indicative of the concentration of the gases in a sample to be measured and includes a light-transmissive surface positioned to be impinged by the monochromatic light beam, a diffusion membrane adapted to be placed in the proximity of a sample and being permeable to a selected gas component thereof, and an indicating substance positioned to be impinged by the monochromatic light beam penetrating the light-transmissive surface and by the gas component penetrating the diffusion membrane. The indicating substance reacts when illuminated by the incident monochromatic light by emitting a resultant light beam having an emitted component which has a color characteristic different from the predetermined color characteristic of the monochromatic light beam. The resultant light beam is conducted away from the indicating substance through the light-transmissive surface. Finally, the emitted component is discriminated from the resultant light beam so that the change in the color characteristic of the indicating substance can be measured and correlated with the concentration of gases in the sample.

27 Claims, 7 Drawing Figures

FIG. 3
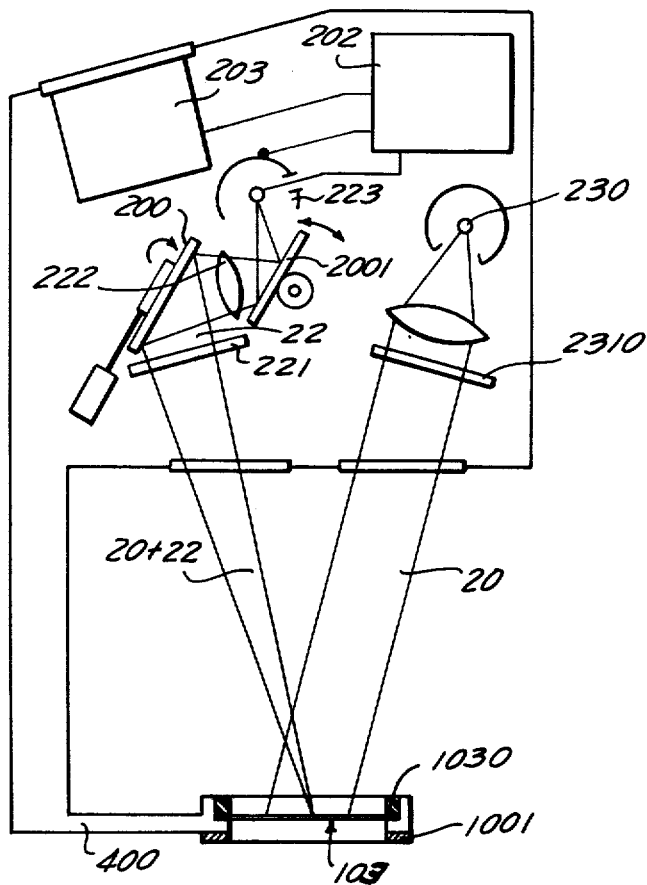
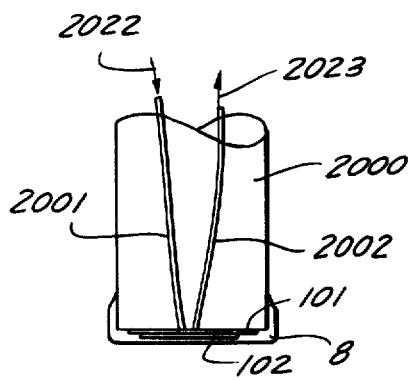
FIG. 4
FIG. 6

METHOD AND ARRANGEMENT FOR MEASURING THE CONCENTRATION OF GASES

BACKGROUND OF THE INVENTION

The present invention relates generally to a method and an arrangement for measuring the concentration of gases in a sample and, more particularly, to a method and an arrangement which optically measures the concentration of oxygen and carbon dioxide dissolved in blood.

It is known in the prior art to provide test cells filled with an indicating substance which reacts with a gas component to be measured in a sample by emitting a fluorescent-type light beam when the indicating substance is illuminated by monochromatic light. When the concentration or distribution of the gas component changes, the indicating substance changes its color characteristic and intensity. In turn this difference in intensity is measured by a light-measuring device. Fluorescent-type indicators are popular because it is relatively simple to filter the fluorescent-type component, thus making possible a high signal-to-noise ratio.

However, fluroescent-type indicators have not been successfully used to measure gases dissolved in the blood stream, because, for example, albumin in the blood interferes with the reaction of the indictor substance.

Thus, the prior art proposed various electrode techniques to measure the concentration of gases. However, such electrode-measuring techniques are possessed of many disadvantages. For example, in the measurement of the partial pressure of oxygen, the polarization-type electrodes must be constituted of very pure material which requires a great deal of costly and frequent maintenance. Moreover, the concentration distribution can only be determined on a point-by-point basis. Even if the prior art electrodes are inserted transcutaneously through the skin, then still only very slight gas quantities ever reach the electrodes. Furthermore, the measurement is strongly influenced by the inherent properties of the electrodes themselves. Since the electrodes require a large amount of gas to flow towards them so as to generate a detectable electrical current, electrode arrangements having large surface areas are impractical. Thus, oxygen concentration distributions are not readily attainable in the prior art.

With respect to the partial pressure measurement of gases other than oxygen, Stow and Randall Amer. J. Physiol. 179/678p —1954 disclose the measurement of carbondioxide with glass electrodes. However, such electrodes require measuring times of over 30 seconds which are undesirably long in most applications. Moreover, the accuracy of the measurement is substantially reduced by the presence of the required reference electrode.

SUMMARY OF THE INVENTION

Accordingly, it is a general object of the present invention to overcome the drawbacks of the prior art.

Another object of the present invention is to provide a method and an arrangement for measuring the concentration of gases in a sample which eliminates the use of electrode-measuring techniques.

Still another object of the present invention is to provide a method and an arrangement for measuring gas concentrations which is relatively maintenance-free.

Yet another object of the present invention is to provide a method and an arrangement for measuring gas concentrations which is fast-acting and universally usable.

A further object of the present invention is to provide a method and an arrangement for measuring gas concentrations which optically shows the entire distribution of the gas in the blood at any one time.

In keeping with these objects and others which will become apparent hereinafter, one feature of the invention resides, briefly stated, in a method and arrangement for measuring the concentration of gases in a sample which comprises means for generating a monochromatic light beam having a predetermined color characteristic. Indicating means are further provided for generating light signals indicative of the concentration of gases in a sample to be measured. The indicating means includes a light-transmissive surface positioned to be impinged by the monochromatic light beam, a diffusion membrane which is adapted to be placed in the proximity of a sample and which is selectively permeable to a gas component thereof, and an indicating substance positioned to be impinged by the monochromatic light beam penetrating the light-transmissive surface and by the gas component penetrating the diffusion membrane. The indicating substance reacts when illuminated by the incident monochromatic light by emitting a resultant light beam having an emitted component which has a color characteristic different from the predetermined color characteristic of the monochromatic light beam. The resultant light beam is conducted away from the indicating substance through the light-transmissive surface, and means for discriminating the emitted component from the resultant light beam is provided so that change in the color characteristic of the indicating substance can be measured and correlated with the concentration of gases in the sample.

In accordance with this feature, the indicating substance reacts very quickly towards an equilibrium condition even with very small quantities of gas being diffused from the sample through the diffusion membrane. This is especially true if the light-transmissive surface is juxtaposed over the diffusion membrane so as to bound a flat, planar space which is ony a few microns thick. The relatively large surface area of the indicating substance permits average measuring values of the gas concentration to be obtained in a relatively short time. A plurality of such thin so-called optodes distributed over an area can be used to measure the distribution of concentration over that area.

Another feature of the invention is that all of the various parts of the arrangement are mounted in a portable housing which can be easily moved towards the place where the sample is to be measured. The housing may also contain additional electrode elements for conducting the resultant electrical signal which is indicative of the gas concentration towards an indicating device.

Still another feature is that one optode can be interchanged in the same arrangement with other optodes which have a different diffusion membrane which is selectively permeable to another gas component to be measured. The interchangeability of the optodes in the portable housing provides for greater versatility.

In accordance with yet another feature, the optode may be constituted not of the aforementioned multi-layered-type construction, but of a supporting foil in which the indicating substance is randomly interspersed and sealingly embedded. The foil itself simultaneously serves as the gas-permeable membrane as well as the light-transmissive surface. This design of the optode insures an especially simple and sturdy construction. The embedding of the indicating substance throughout the foil is obtained by conventional chemical and physio-chemical techniques, preferably by polymerization of a solution of silicon or any synthetic plastic material such as polyvinylchloride mixed with the indicating substance.

An additional feature of the invention resides in controlling the temperature at which the gas is measured. Heating and/or cooling coils, heat exchangers, or Peltier-type elements, or the like, can be employed to control the temperature of the gas. If the heat input necessary for effecting a temperature change in the sample is measured, the perfusion rate of the sample can also be determined.

The means for generating light signals indicative of the concentration of gases may comprise one or more adjacent optodes, each containing a different indicating substance; or a single optode having separate sections, each of which contains its own respective indicating substance; or a single supporting foil having separate indicating subtances embedded therein. It is especially desirable if a pair of optodes are used transcutaneously to measure the partial pressure of oxygen and/or carbondioxide being diffused from a blood vessel through the surrounding skin. The optodes may, in accordance with the invention, be arranged in the free end of a catheter having light-conductive fibers which convey light beams towards and away from the optodes. The cathater can be arranged then directly in a vein or artery. If two optodes are employed, then the incident light beam contains two monochromatic components which are subsequently separately processed. The use of two simultaneously acting optodes overcomes the prior art disadvantage of having to separately measure the oxygen and carbondioxide gas concentrations at separate times at one location on the skin.

Still another feature of the arrangement is to arrange the indicating substance in dichroic layers so as to absorb the incoming monochromatic light beam and reduce scattered radiation effects.

Also, it is desirable to provide a reflective surface on the inner side of the diffusion membrane, or on the inner side of a wall placed behind the diffusion membrane, in order to direct the monochromatic light beam twice through the indicating substance. This is especially desirable if the monochromatic light beam does not have sufficient strength or purity to illuminate the indicating substance.

On the other hand, if sufficient energy and purity is provided in the incoming monochromatic light beam, the diffusion membrane or the wall placed behind the same can be darkened or provided with a light-absorbing layer so as to reduce scatter.

If the optode is formed with a large light-impinging surface area, cross-diffusion is substantially reduced by providing for fine, subdivided groups of optodes.

Still another feature of the invention resides in using very small optodes in particle form, each containing indicator substance. These particles can then be introduced into the sample. Such a measuring method is extremely fast-acting since the combined outer surface areas of all the particles is quite high.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIG. 3 is still another diagrammatic view of an additional embodiment according to the present invention;

FIG. 4 is an enlarged, partial diagrammatic view of a detail of the arrangement;

FIG. 6 is a bottom view of the catheter illustrated in FIG. 5.

DESCRIPTION OF THE PREFERRED EMBODIMENTS

Figure 1:
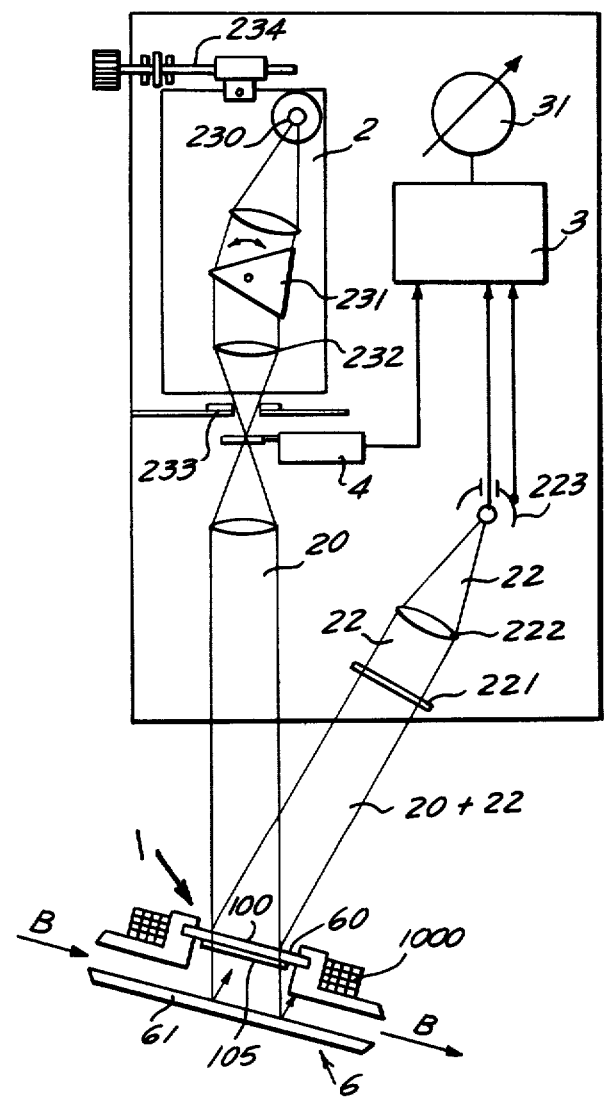
FIG. 1 is a diagrammatic view of a first embodiment in accordance with the present invention.

Referring firstly to the FIG. 1 of the drawing, this illustrated embodiment for measuring gases in a sample comprise means 2 for generating a monochromatic light beam. Light emanating from a light source 230 is focussed by lens element 232 onto a light-dispersion prism 231. The resulting beam is split up into its spectral components and focussed by another lens element 232 towards the exit opening or aperture 233.

In order to select one of the spectral components to serve as a source of monochromatic light, i.e. a light beam having substantially a single frequency and wavelength, an adjusting arrangement comprising an adjusting screw 234 is provided. By turning screw 234, the entire monochromatic light arrangement is moved and thereby the desired wavelength can be obtained through the aperture 233.

The monochromatic light beam generally identified by reference numeral 20 is directed towards a so-called "optode 1". The optode generates the light signal which is indicative of the concentration of the gases in a sample. Optode 1 is composed of an upper layer 60 having a light-transmissive surface positioned to be impinged by the monochromatic beam 20, and a juxtaposed lower diffusion membrane 105. The layer 60 and the membrane 105 together bound a space for an indicating substance 100. The membrane 105 is chosen so that it is permeable to a selected gas component of the sample being measured. If the indicating substance 100 is a liquid, it is preferable if the membrane 105 and the layer 60 are fluid-tightly sealed relative to each other.

The indicating substance 100 is positioned in the optode 1 so that it is impinged by a major portion of the monochromatic light beam 20 which penetrates the light-transmissive layer 60. Moreover, when illuminated by the beam 20, the substance 100 reacts with the gas component which penetrates the diffusion membrane 105 and changes its color characteristic. Specifically, the substance 100 emits a fluorescent-type beam whose color and intensity is different from the color characteristic of the monochromatic light beam.

The resultant light beam emanating from the optode is comprised of two components 20 and 22. Component 20 is essentially composed of the monochromatic light beam being reflected from the indicating substance and/or the light-transmissive layer 60. COmponent 22 is the fluorescent light signal emitted by the substance 100 itself.

The resultant beam is then conducted away from the indicating substance 100 through the light-transmissive layer 60 so that information contained in component 20 and 22 can be discriminated from component 20 and used to yield the desired information as to the concentration of the gas currently being measured in the sample.

This discrimination process can occur in many ways. For example, in FIG. 1, if an especially pure monochromatic signal is desired (i.e. a monochromatic signal having predominantly a single frequency) then a very slight apertural width is provided for the exit opening 233. In addition, it is advantageous if a modulator 4 having a movable shutter is positioned in the path of the incident monochromatic light beam 20 so as to repeatedly interrupt beam 20 and vary its intensity at a predetermined frequency. (At the same time the modulator 4 generates an electrical signal which has the frequency of interruption of the light to be used in the amplifier-demodulator unit 3 for phase sensitive demodulation of the light signal.) The monochromatic light beam then receives the intelligence at the optode so that, when the resultant light beam is passed through the filter 221, only the component 22 remains. Component 22 is thereupon focussed by lens 222 onto the photocell or receiver 223, whereupon the receiver conveys the information to be processed in known manner to the relatively stable and preferably noiseless electronic amplifier-demodulator unit 3, which is preferably phase-sensitive. The resulting information signal is then conducted to a display instrument 31.

In use, the optode 1 is placed so that the membrane 105 is in direct contact with the sample. For example, if the sample is blood, then the blood B can be passed through a flow-through chamber 6. An upper side of the chamber 6 is constituted by the optode 1; a bottom opposite side of the chamber is generally identified by reference numeral 61. If the concentration of the gas in the blood to be measured changes, then the amount of gas being diffused through membrane 105 will correspondingly change. This, of course, means that the strength or intensity of the fluorescent-type emitted light component 22 will also change. This change in color characteristic will then be sensed and displayed on the display instrument 31 which can serve either as a direct or differential read-out device.

If it is desired to employ a plurality of monochromatic light beam components, then each monochromatic component can be provided with its own modulator that is operative at different respective frequencies. Each frequency after being received by the photocell can be processed in the same electronic unit and be individually separated and displayed by using the respective electrical signals for phase sensitive demodulation.

In case it is desired to control the temperature of the sample during the measurement, the temperature-control means 1000 is placed in the proximity of the sample for cooling and/or heating the latter. In FIG. 1, the temperature-controlling means 1000 is configurated as an annular coil surrounding the optode and is in heat-exchange relationship with the blood B. If the temperature information is processed with the gas-concentration information, then the perfusion rate is determinable.

In order to increase the strength and intensity of the emitted light component 22, it is very desirable to provide a reflective surface at the inner side of the bottom wall 61 of the flow-through chamber 6 so that the incident monochromatic light beam will pass twice through the indicating substance 100. In this case it is advantageous if small apertural widths are provided at the monochromatic arrangement 2, or if the indicating substance 100 is arranged in dichroic layers.

If, on the other hand, the purity and strength of the monochromatic light component is adaquate for exciting the indicating substance 100 to produce an emitted light component of sufficient strength, then it is desirable to provide an absorbing layer on the inner side of the bottom wall 61. Thus, instead of providing a mirror-like surface as in the above-mentioned case, the bottom wall is blackened. This is advantageous in reducing scatter radiation caused by the incoming monochromatic beam so that the outgoing resultant beam is essentially comprised of relatively more emitted light component 22 and less of the reflected light component 20.

Figure 2:
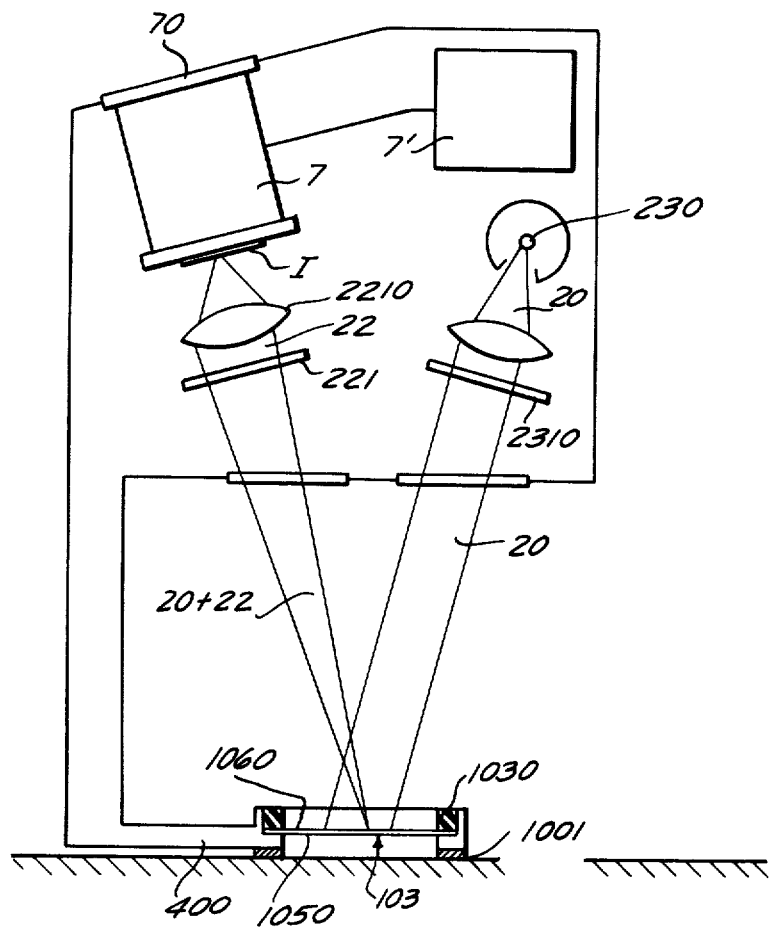
FIG. 2 is a diagrammatic view of still another embodiment in accordance with the present invention.
Figure 2A:
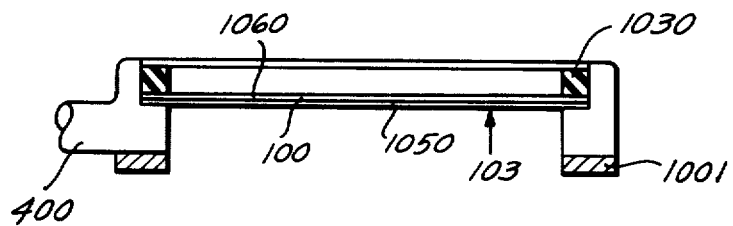
FIG. 2a is an enlarged view of a detail of FIG. 2

Turning now to the embodiment of FIG. 2, the means for generating monochromatic light is simplified from the arrangement shown in FIG. 1 and is provided with a light source 230 which projects at its light onto a lens which, in turn, directs the light through a monochromatic filter 3210. Filter 2310 is operative for allowing substantially only the desired monochromatic light beam 20 to pass therethrough towards the optode 103.

Optode 103 is analogous to optode 1 as discussed in FIG. 1 and is similarly provided with light-transmissive surface 1060, indicating substance 100 and gas-permeable membrane 1050. One essential difference, however, relates to the placement of the optode and the size thereof with respect to the sample. In FIG. 1, a flow-through chamber 6 was used; in the present case, the membrane 1050 is positioned a very slight distance from a tissue or skin or like object O so that gas diffusing therefrom penetrates the membrane 1050 and reacts with the indicating substance 100. Optode 103 is preferably annular and clamped in position by clamping ring 1030 which is provided in housing bracket arm 400. It is advantageous if the ring 1030 is removable so that different optrodes, each adapted to measure a different gas component, can be interchanged as desired. In order to insure that the diffused gas is directed towards membrane 1050, sealing means 1001 is provided intermediate optode 103 and the object O.

The resultant light beam again has two components, and the emitted fluorescent-type light component 22 is discriminated from the reflected component 20 by passing the resultant beam through a filter 221 which serves to pass substantially only the light component 22. Lens 2210 focusses the light component 22 onto an image area I. Thereupon, the image-amplifier arrangement 7 with the high voltage source 7' electronically produces an electrono-optic image on the display screen 70.

Thus, this device can display a stationary or static concentration distribution of a gas being measured. Of course, the display must be previously calibrated to account for the particular indicating substance being used, the particular gas being measured, the distance of the optode from the object, the size of the optode, etc.

If the indicating substance is subdivided into layers to reduce cross-diffusion, this fact must also be taken into consideration. The display of the image on a screen can be permanently recorded by using a camera or like image-recording device.

Instead of forming the optode as a sealed multi-layered construction, i.e. upper light-transmissive layer (60 or 1060), a lower diffusion membrane (105 or 1050), and a middle layer of indicating substance 100, the optodes for all of the previously disclosed embodiments may be constituted of a supporting foil in which the indicator substance is sealingly embedded. The foil is generally constituted of any gas-diffusable material, such as a solution of silicon or any synthetic plastic material such as polyvinylchloride randomly mixed with the indicating substance preferably in a polymerization-type reaction. The indicating substance is so strongly embedded in the supporting foil that, even if it were placed in direct contact with the blood in flow-through chamber 6 of FIG. 1, the indicating substance would not be washed away.

Besides the planar configurations of the optodes or supporting foil, each can be adapted to conform to the particular configuration of the object being measured. Thus, the optodes may comprise a plurality of very small carrier particles having the indicating substance embedded therein and which are added to a carrier fluid containing the gas to be measured for instance to the blood.

Turning to FIG. 3, this embodiment is essentially analogous to the one described in connection with FIG. 2 except that the discrimination process is different. The resultant beam is again passed through a filter 221 which serves to screen out the reflected light component 20. The fluorescent light component 20 is then scanned by a first swinging mirror 200 in one direction, and then directed by lens 222 towards a second swinging mirror 201 whereupon another scan is taken in a mutually normal direction. Thus an areal scan is furnished. The information contained in the scanning of the optode is then conveyed to a photoelectric element 223, whereupon the information is conducted towards an amplifier 202 and coverted into an electrono-optic image or raster which can be viewed at the display screen 70 of the viewing apparatus 203.

In FIG. 4, the incident monochromatic light beam and the outgoing resultant beam are respectively directed towards and away from one or more optodes by means of light-conductive fibers 2001 and 2002 of a light-conductive cable 2000. Light-conductive fiber 2001 has its input end 2022 connected to a source of monochromatic light so that the latter is thereby brought to the optode whereupon it impinges on the indicating substance. The free end of light-conductive cable 2000 is sealingly covered with the gas-permeable membrane 8 so that the gas being measured can penetrate the membrane and react with the indicating substance. The emitted light is conducted by light-conductive cable 2003 towards its output end 2023 to a discrimination arrangement.

The light fibers may be connected to either one or more optodes and, as shown in FIG. 4, fiber 2001 is used to illuminate a pair of adjacent optodes 101 and 102 which lie behind each other as viewed in direction into the plane of FIG. 4. Moreover, each optode may be used to measure the same gas component, or preferably different gas components when their respective gas-permeable membranes are selected accordingly.

The inner surface of the gas-permeable membrane 8 can be provided with a reflective coating in case an increase in the illumination of the indicating substance by the monochromatic light is required; alternatively, the inner surface may be provided with a blackened coating in order to reduce scatter radiation. Of course, light-scattering not eliminated thereby can also be reduced and substantially eliminated by electrical means in the amplifier circuitry.

Figure 5:
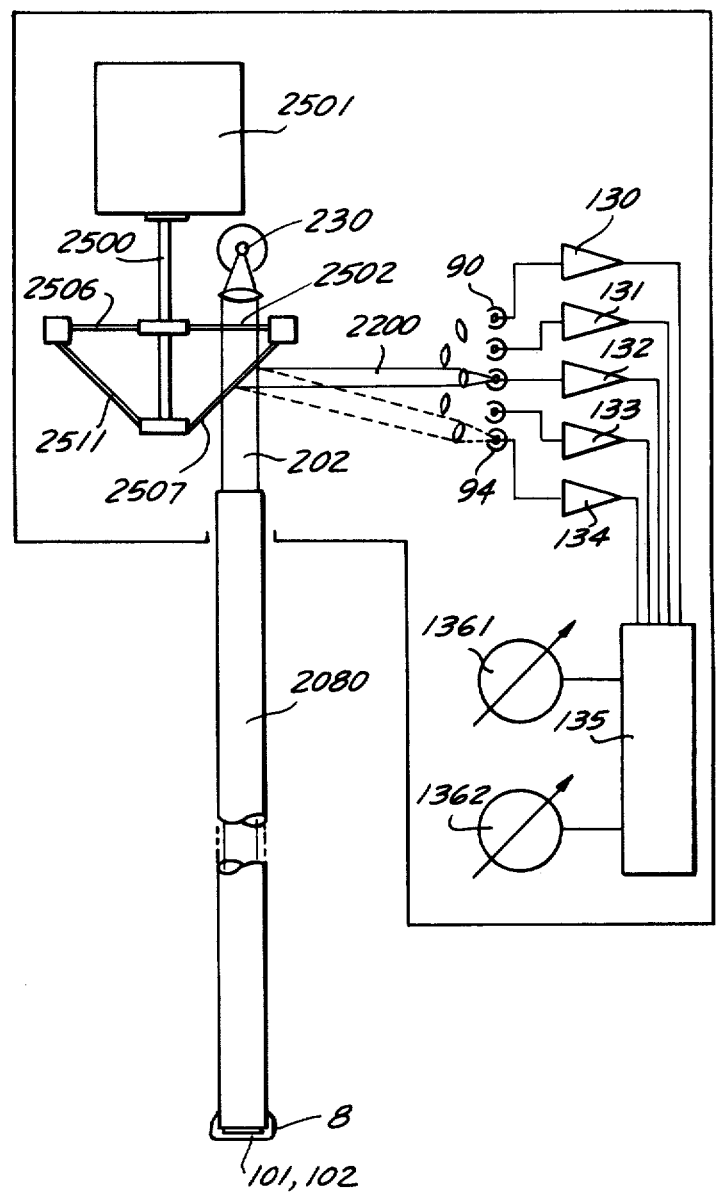
FIG. 5 is a diagrammatic of still another embodiment in accordance with the present invention which uses the modification illustrated in FIG. 4.

FIG. 5 shows an embodiment of a multiple analysis-type measuring device using the concept disclosed in FIG. 4. The light-conductive cable 2080 is housed in a catheter whose free end is provided with optodes 101 and 102 and covered by membrane 8. The measurement is advantageous since obtaining a plurality of separate readings, each of which is later processed to produce a final result, is more accurate as compared with a single mesurement device according to Pflugers Archiv 342/41—60/1973. With this method it is possible to account for optical interferences, white light effects, single measurement errors, etc.

In accordance with the invention, light source 230 directs a light beam 202 towards the input end of cable 2080. Beam 202 is modulated by a rotating assembly wheel which comprises a drive 2501 which turns shaft 2500. A first set of five monochromatic filters 2502–2506 are mounted on the shaft 2500 so as to intercept beam 202 in normal direction; a second set of single frequency light filtering elements 2507–2511 is mounted on the shaft 2500 so as to subsequently intercept beam 202 at angles of approximately 45°. The second set of light elements 2507–2511 is partially mirrored and so positioned that the resultant beams returning from the optodes 101, 102 are sequentially reflected towards photocells 90–94. Each photocell converts the respective light signals into a corresponding electrical signal which is then respectively amplified in amplifiers 130–134. The plurality of electrical signals are processed together in an analyzer unit 135 which combines the separate signals in a manner disclosed by Pflugers, Archiv 342/41—60/1973. The display instruments 1361 and 1362 respectively indicate the gas concentrations detected by the optodes 101, 102. Thus, optical interference caused by the optodes or by the blood itself, white light, and additive color effects from the indicating substance are substantially elimimated.

By placing the optodes 101, 102 directly behind each other, it is possible to make the free end of the catheter-type cable very thin so that the latter can be used to measure gas components directly even in very small blood vessels.

FIG. 6 illustrates an embodiment especially useful when the optode is directly applied against the skin. Optode 1031 is comprised of two adjacent membranes 110 and 111. Membrane 110 is selected to be permeable to oxygen; and membrane 111 is selected to be permeable to carbondioxide. Then, these two gas components can be simultaneously measured.

As examples of typical indicating substances, $\beta$-methyl-umbelliferon can be used to directly measure the pH value of the blood being measured from which the carbon-dioxide value can be determined by the use of a nomograph; in addition, pyrene butyric acid can be directly used to measure the oxygen concentration of the sample.

It will be understood that each of the elements described above, or two or more together, may also find a useful application in other types of constructions differing from the types described above.

While the invention has been illustrated and described as embodied in a method and arrangement for measuring the concentration of gases, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of this invention.

What is claimed as new and desired to be protected by Letters Patent is set forth in the appended claims.

We claim:

1. A method of measuring the concentration of gases in a sample comprising the steps of generating a monochromatic light beam having a predetermined color characteristic; generating light signals indicative of the concentration of gases in a sample to be measured by positioning an indicator having a light-transmissive surface positioned to be impinged by said monochromatic light beam, a diffusion membrane adapted to be placed in the proximity of a sample and being selectively permeable to a gas component thereof, and an indicating substance positioned to be impinged by the monochromatic light beam penetrating said light-transmissive surface and by said gas component penetrating said diffusion membrane, said indicating substance reacting when illuminated by said incident monochromatic light beam by emitting a resultant light beam having an emitted component which has a color characteristic different from said predetermined color characteristic; conducting said resultant light beam away from said indicating substance through said light-transmissive surface; and discriminating said emitted component from said resultant light beam so that the change in the color characteristic of said indicating substance can be measured and correlated with the concentration of gases in the sample.

2. In an arrangement for measuring the concentration of gases in a sample, a combination comprising means for generating a monochromatic light beam having a predetermined color characteristic; indicating means for generating light signals indicative of the concentration of gases in a sample to be measured, including a light-transmissive surface positioned to be impinged by said monochromatic light beam, a diffusion membrane adapted to be placed in proximity of a sample and being permeable to a selected gas component thereof, and an indicating substance positioned to be impinged by said monochromatic light beam penetrating said light-transmissive surface and by said gas component penetrating said diffusion membrane, said indicating substance reacting when illuminated by said incident monocrhromatic light beam by emitting a resultant light beam having an emitted component which has a color characteristic different from said predetermined color characteristic; means for conducting said resultant light beam away from said indicating substance through said light-transmissive surface; and means for discriminating said emitted component from said resultant light beam so that the change in the color characteristic of said indicating substance can be measured and correlated with the concentration of gases in the sample.

3. The arrangement of claim 2, wherein said indicating substance is sealingly embedded thoughout said diffusion membrane.

4. The arrangement of claim 2; and further comprising means for controlling the temperature of a sample.

5. The arrangement of claim 2, wherein the indicating substance is $\beta$-methyl-umbelliferon.

6. The arrangement of claim 2, wherein the indicating substance is Pyrene-butyric acid.

7. The arrangement of claim 2; and further comprising additional indicating substances intermixed with said first-mentioned indicating substance.

8. The arrangement of claim 2; and further comprising a reflecting wall located behind said membrane.

9. The arrangement of claim 2; and further comprising an absorption wall located behind said membrane.

10. The arrangement of claim 2, wherein sid discriminating means comprises filtering means for permitting substantially only said emitted light to pass through.

11. The arrangement of claim 2, wherein said indicating means is comprised of a plurality of particles, each comprising said indicating substance and said diffusion membrane.

12. The arrangement of claim 2; and further comprising additional indicating means adjacent said first-mentioned indicating means, said additional indicating means having a diffusion membrane selectively permeable to another gas component and an indicating substance which reacts with the latter.

13. The arrangement of claim 12, wherein the diffusion membrane of said first-mentioned indicating means is substantially permeable to oxygen; and wherein the diffusion membrane of said additional indicating means is substantially permeable to carbon-dioxide.

14. The arrangement of claim 2; wherein said means for generating said monochromatic light beam includes a light-conductive cable for directing said monochromatic light beam towards said indicating means; and wherein said conducting means comprises another light-conductive cable for directing said resultant light beam away from said indicating means.

15. The arrangement of claim 14; and further comprising additional indicating means located adjacent said first-mentioned indicating means; and wherein said monochromatic light beam comprises two monochromatic components, each being directed by said one light-conductive cable towards said respective indicating means.

16. The arrangement of claim 15, and wherein both said indicating means respectively emit emitted light components, each being conducted by said other light-conductive cable towards said discrimination means so that each emitted light component is individually measured.

17. The arrangement of claim 2; and further comprising a portable housing containing said means for generating a monochromatic light beam and said discrimination means for transporting the measuring arrangement to a sample.

18. The arrangement of claim 17, wherein said indicating means is interchangeably mounted in said housing.

19. The arrangement of claim 17; and further comprising additional measuring electrodes mounted in said housing.

20. The arrangement of claim 2, wherein said light-transmissive surface is planar and constitutes an upper layer, and wherein said indicating substance is generally located in a plane intermediate said upper layer and said diffusion membrane.

21. The arrangement of claim 20, wherein said indicating substance is arranged in a dichroic layer having one side which absorbs said monochromatic light beam.

22. The arrangement of claim 20, wheren said membrane has a reflective layer on its side facing said indicating substance.

23. The arrangement of claim 20, wherein said membrane has an absorbing layer on its side facing said indicating substance.

24. The arrangement of claim 2, wherein said means for generating a monochromatic light beam includes means for modifying the latter into a plurality of separate monochromatic components, each monochromatic component being directed towards said indicating substance.

25. The arrangement of claim 24, wherein said modifying means comprises a plurality of monochromatic filters, each positioned to be impinged by said monochromatic light beam.

26. The arrangement of claim 24, wherein said conducting means comprises a plurality of light-reflective elements, each positioned to be impinged by said emitted light component.

27. The arrangement of claim 26, wherein said discriminating means processes each of said emitted light components.

* * * * *